US007375525B2

(12) United States Patent
Laubacher et al.

(10) Patent No.: US 7,375,525 B2
(45) Date of Patent: May 20, 2008

(54) USE OF MULTIPLE SENSORS IN A NUCLEAR QUADROPOLE RESONANCE DETECTION SYSTEM TO IMPROVE MEASUREMENT SPEED

(75) Inventors: Daniel B. Laubacher, Wilmington, DE (US); James D. McCambridge, Swarthmore, PA (US); Charles Wilker, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/013,591

(22) Filed: Dec. 15, 2004

(65) Prior Publication Data

US 2008/0094061 A1    Apr. 24, 2008

Related U.S. Application Data

(60) Provisional application No. 60/529,991, filed on Dec. 15, 2003.

(51) Int. Cl.
  *G01V 3/00*    (2006.01)
(52) U.S. Cl. .................................... 324/318
(58) Field of Classification Search ......... 324/300–322
  See application file for complete search history.

(56) References Cited

U.S. PATENT DOCUMENTS

| | | | |
|---|---|---|---|
| 3,373,348 A | 3/1968 | Vanier et al. | |
| 3,764,892 A | 10/1973 | Rollwitz | |
| 4,027,768 A | 6/1977 | Riessen | |
| 4,072,768 A | 2/1978 | Fraser et al. | |
| 4,514,691 A | 4/1985 | De Los Santos et al. | |
| 5,036,279 A * | 7/1991 | Jonsen ........................ | 324/307 |
| 5,206,592 A | 4/1993 | Buess et al. | |
| 5,233,300 A | 8/1993 | Buess et al. | |
| 5,258,710 A | 11/1993 | Black et al. | |
| 5,262,394 A | 11/1993 | Wu et al. | |
| 5,276,398 A | 1/1994 | Withers et al. | |
| 5,351,007 A | 9/1994 | Withers et al. | |
| 5,418,213 A | 5/1995 | Tanaka et al. | |
| 5,457,385 A | 10/1995 | Sydney et al. | |
| 5,583,437 A | 12/1996 | Smith et al. | |
| 5,585,723 A | 12/1996 | Withers | |
| 5,592,083 A | 1/1997 | Magnuson et al. | |
| 5,594,338 A | 1/1997 | Magnuson | |
| 5,656,937 A | 8/1997 | Cantor | |
| 5,661,400 A | 8/1997 | Plies et al. | |
| 5,750,473 A | 5/1998 | Shen | |
| 5,751,146 A | 5/1998 | Hrovat | |
| 5,804,967 A | 9/1998 | Miller et al. | |
| 5,814,987 A | 9/1998 | Smith et al. | |
| 5,814,989 A * | 9/1998 | Smith et al. ................. | 324/300 |
| 5,814,992 A | 9/1998 | Busse-Gracitz et al. | |
| 5,872,080 A | 2/1999 | Arendt et al. | |
| 5,952,269 A | 9/1999 | Ma et al. | |
| 5,973,495 A | 10/1999 | Mansfield | |
| 5,986,455 A | 11/1999 | Magnuson | |
| 5,999,000 A | 12/1999 | Srinivasan | |
| 6,025,719 A | 2/2000 | Anderson | |
| 6,054,856 A | 4/2000 | Garroway et al. | |
| 6,088,423 A | 7/2000 | Krug et al. | |
| 6,091,240 A | 7/2000 | Smith et al. | |
| 6,104,190 A | 8/2000 | Buess et al. | |
| 6,108,569 A | 8/2000 | Shen | |
| 6,150,816 A | 11/2000 | Srinivasan | |
| 6,166,541 A | 12/2000 | Smith et al. | |
| 6,169,399 B1 | 1/2001 | Zhang et al. | |
| 6,194,898 B1 | 2/2001 | Magnuson et al. | |
| 6,201,392 B1 | 3/2001 | Anderson et al. | |
| 6,218,943 B1 | 4/2001 | Ellenbogen | |
| 6,242,918 B1 | 6/2001 | Miller et al. | |
| 6,291,994 B1 * | 9/2001 | Kim et al. ................... | 324/300 |
| 6,335,622 B1 | 1/2002 | James et al. | |
| 6,370,404 B1 | 4/2002 | Shen | |
| D459,245 S | 6/2002 | Power | |
| 6,420,872 B1 | 7/2002 | Garroway et al. | |
| 6,486,838 B1 | 11/2002 | Smith et al. | |
| 6,538,445 B2 | 3/2003 | James et al. | |
| 6,541,966 B1 | 4/2003 | Keene | |
| 6,556,013 B2 | 4/2003 | Withers | |
| 6,566,873 B1 | 5/2003 | Smith et al. | |
| 6,590,394 B2 | 7/2003 | Wong et al. | |
| 6,617,591 B1 | 9/2003 | Simonson et al. | |
| 6,653,917 B2 | 11/2003 | Kang et al. | |
| 6,751,489 B2 | 6/2004 | Shen | |

(Continued)

FOREIGN PATENT DOCUMENTS

EP    0 426 851    5/1991

(Continued)

OTHER PUBLICATIONS

Garroway, et al., "Remote Sensing By Nuclear Quadrupole Resonance", IEEE Transactions on Geoscience and Remote Sensing, Jun. 2001, pp. 1108-1118, vol. 39, No. 6.

(Continued)

*Primary Examiner*—Brij Shrivastav
*Assistant Examiner*—Dixomara Vargas

(57) ABSTRACT

The use of multiple sensors improves the measurement speed of a nuclear quadrupole resonance detection system when the nuclear quadrupole resonance frequency is known only within a range of frequencies.

24 Claims, No Drawings

U.S. PATENT DOCUMENTS

| | | |
|---|---|---|
| 6,751,847 B1 | 6/2004 | Brey et al. |
| 6,777,937 B1 | 8/2004 | Miller et al. |
| 6,819,109 B2 | 11/2004 | Sowers et al. |
| 6,822,444 B2 | 11/2004 | Lai |
| 6,847,208 B1 | 1/2005 | Crowley et al. |
| 6,952,163 B2 | 10/2005 | Muey et al. |
| 6,956,476 B2 | 10/2005 | Buess et al. |
| 6,958,608 B2 | 10/2005 | Takagi et al. |
| 7,049,814 B2 | 5/2006 | Mann |
| 7,106,058 B2 | 9/2006 | Wilker et al. |
| 2002/0068682 A1 | 6/2002 | Shen |
| 2002/0153891 A1 | 10/2002 | Smith et al. |
| 2002/0156362 A1 | 10/2002 | Bock et al. |
| 2002/0169374 A1 | 11/2002 | Jevtic |
| 2002/0190715 A1 | 12/2002 | Marek |
| 2003/0020533 A1 | 1/2003 | Gao et al. |
| 2003/0062896 A1 | 4/2003 | Wong et al. |
| 2003/0071619 A1 | 4/2003 | Sauer et al. |
| 2003/0119677 A1 | 6/2003 | Qiyan et al. |
| 2003/0136920 A1 | 7/2003 | Flores et al. |
| 2004/0124840 A1 | 7/2004 | Reykowski |
| 2004/0222790 A1 | 11/2004 | Karmi et al. |
| 2004/0251902 A1 | 12/2004 | Takagi et al. |
| 2005/0104593 A1 | 5/2005 | Laubacher et al. |
| 2005/0122109 A1 | 6/2005 | Wilker |
| 2005/0140311 A1 | 6/2005 | Alvarez |
| 2005/0148331 A1 | 7/2005 | Flexman et al. |
| 2005/0206382 A1 | 9/2005 | Laubacher et al. |
| 2005/0248345 A1* | 11/2005 | Alvarez et al. ............. 324/310 |
| 2005/0258831 A1* | 11/2005 | Alvarez et al. ............. 324/310 |
| 2005/0264289 A1* | 12/2005 | Alvarez et al. ............. 324/310 |
| 2005/0270028 A1 | 12/2005 | Alvarez |
| 2006/0012371 A1 | 1/2006 | Laubacher et al. |
| 2006/0038563 A1 | 2/2006 | Cisholm et al. |
| 2006/0082368 A1 | 4/2006 | McCambridge |
| 2006/0119360 A1 | 6/2006 | Yamamoto et al. |

FOREIGN PATENT DOCUMENTS

| | | |
|---|---|---|
| EP | 1 122 550 A1 | 8/2001 |
| EP | 1 168 483 | 1/2002 |
| EP | 1 416 291 | 5/2004 |
| EP | 1 477 823 A | 11/2004 |
| GB | 2 286 248 | 8/1995 |
| GB | 2 289 344 | 11/1995 |
| JP | 05 269108 | 10/1993 |
| JP | 07 265278 | 10/1995 |
| WO | WO 92/17793 | 10/1992 |
| WO | WO 92/17794 | 10/1992 |
| WO | WO 92/19978 | 11/1992 |
| WO | WO 92/21989 | 12/1992 |
| WO | WO 94/05022 | 3/1994 |
| WO | WO 95/34096 | 12/1995 |
| WO | WO 96/39636 | 12/1996 |
| WO | WO 96/39638 | 12/1996 |
| WO | WO 98/37438 | 8/1998 |
| WO | WO 98/54590 | 12/1998 |
| WO | WO 99/45409 | 9/1999 |
| WO | WO 99/50689 | 10/1999 |
| WO | WO 00/70356 | 11/2000 |
| WO | WO 01/85811 | 11/2001 |
| WO | WO 02/082115 A2 | 10/2002 |
| WO | WO 02/098364 | 12/2002 |
| WO | WO 03/014700 | 2/2003 |
| WO | WO 03/040761 | 5/2003 |
| WO | WO 03/096041 | 11/2003 |
| WO | WO 2004/001454 A | 12/2003 |
| WO | WO 2004/102596 | 11/2004 |
| WO | WO 05/059582 A1 | 6/2005 |

OTHER PUBLICATIONS

Garroway, et al., "Narcotics and Explosives Detection by 14N pure NQR", SPIE, 1993, pp. 318-327, vol. 2092, Maryland.

Hirschfeld, et al., "Short Range Remote NQR Measurements", Journal of Molecular Structure, 1980, pp. 63-77, vol. 58, The Netherlands.

Kushida, et al., "Dependence on the Pure Quadrupole Resonance Frequency on Pressure and Temperature", Physical Review, (Dec. 1956), pp. 1364-1377, vol. 104, No. 5, Massachusetts.

Vanier, "Temperature Dependence of the Pure Nuclear Quadrupole Resonance Frequency in KCI03", Canadian Journal of Physics, (Nov. 1960), pp. 1397-1405, vol. 38, No. 11, Canada.

Smith, et al., "Nitrogen Electric Quadrupole and Proton Magnetic Resonances in Thiourea", Journal of Chemical Physics, (Oct. 1964), pp. 2403-2416, vol. 41, No. 8, New York.

Miller, et al., "Performance of a High-Termperature Superconducting Probe for In Vivo Microscopy at 2.0 T", Magnetic Resonance in Medicine, (1999) pp. 72-79, vol. 41.

W.H. Wong, et al., "HTS Coils for High Resolution Nuclear Magnetic Resonance Spectroscopy", Advances in Cryogenic Engineering, (1996), pp. 953-959, New York.

V. Kotsubo et al., "Cryogenic System for a High Temperature Superconductor NMR Probe", Advances in Cryogenic Engineering, Jul. 17, 1995, vol. 41, pp. 1857-1864, New York.

Kushida, et al., "Dependence on the Pure Quadrupole Resonance Frequency on Pressure and Temperature", Physical Review, (Dec. 1956), pp. 1364-1377, vol. 104, No. 5, Massachusetts.

Vanier, "Temperature Dependence of the Pure Nuclear Quadrupole Resonance Frequency in KC103", Canadian Journal of Physics, (Nov. 1960), pp. 1397-1405, vol. 38, No. 11, Canada.

Smith, et al., "Nitrogen Electric Quadrupole and Proton Magnetic Resonances in Thiourea", Journal of Chemical Physics, (Oct. 1964), pp. 2403-2416, vol. 41, No. 8, New York.

Turner, C.W., High temperature superconductor circuit components for cryogenic microwave systems, Electrical and Computer Engineering, 1993, Canadian Conference on Vancouver, BC Canada (Sep. 14-17, 1993) Sep. 14, 1993 XP 010118071.

W. A. Edelstein et al., A signal-to-noise calibration procedure for NMR imaging systems, Medical Physics, vol. 11 (2) Mar./Apr. 1984, pp. 180-185.

Hirschfeld, et al., "Short Range Remote NQR Measurements", Journal of Molecular Structure, 1980, pp. 63-77, vol. 58, The Netherlands.

Garroway, et al., "Remote Sensing By Nuclear Quadrupole Resonance", IEEE Transactions on Geoscience and Remote Sensing, Jun. 2001, pp. 1108-1118, vol. 39, No. 6.

Garroway, et al., "Narcotics and Explosives Detection by 14N pure NQR", SPIE, 1993, pp. 318-327, vol. 2092, Maryland.

Charles Wilker, "HTS Sensors for NQR Spectroscopy", vol. 1, pp. 143-146, 2004.

Anders Stensgaard, "Optimized Design of the Shielded-Loop Resonator", Journal of Magnetic Resonance, 122, 120-126 (1996), Article No. 0187.

He, D.F. et al., "Metal detector based on high-Tc RF SQUID", Physics C 378-381 (2002).pp. 1404-1407.

Bendall, et. al., "Elimination of Coupling between Cylindrical Transmit Coils and Surface-Receive Coils for in Vivo NMR" Magnetic Resonance in Medicine v3 p. 157-163, 1986.

Black, et al., "A High-Temperature Superconducting Receiver For Nuclear Magnetic Resonance Microscopy", Science, vol. 259, pp. 793-795 Feb. 5, 1993.

Black, et al., "Performance Of A High-Temperature Superconducting Resonator For High-Field Imaging", Journal Of Magnetic Resonance, pp. 74-80 (1995).

Colton, et. al., "Making the World a Safer Place", Science, v.299, i.5611, Pgd.1324-1325, Feb. 2006.

Fisher, et al., "A Versatile Computer-Controlled Pulsed Nuclear Quadrupole Resonance Spectrometer", Review of Scientific Instruments, v70, No. 12, p. 4678, Dec. 1999.

Hill, "Improved Sensitivity of NMR Spectroscopy Probes By Use Of High-Temperature Superconductive Detection Coils", IEEE Transactions On Applied Superconductivity, vol. 7, pp. 3750-3753, Jun. 1997.

Roemer, et. al., "The NMR Phased Array", Magnetic Resonance In Medicine 16, pp. 192-225, 1990.

Withers, et al., "Thin-Film HTD Probe Coils For Magnetic-Resonance Imaging", IEEE Transactions On Applied Superconductivity, vol. 3, pp. 2450-2453, Mar. 1993.

Landers, et al., "Electric Effects and Molecular Motion in β-Octahydro-1,3,5,7-tetranitro-1,3,5,7-tetrazocine Bases on $^{14}N$ Nuclear Quadrupole Resonance Spectroscopy", American Chemical Society, J. Phys. Chem., 85, pp. 2616-2623, 1981.

Karpowicz, et. Al., "Librational Motion of Hexahydro-1,3,5-trinitro-s-triazine Based on the Temperature Dependence of the Nitrogen-14 Nuclear Quadrupole Resonance Spectra: The Relationship to Condensed-Phase Thermal Decomposition", American Chemical Society, J. Phys. Chem. 87, pp. 2109-2112, 1983.

Volpicelli, et. al., "Locked rf Spectrometer for Nuclear Quadrupole Resonance", The Review of Scientific Instruments, v.25, No. 2, pp. 150-153, Feb. 1965.

Benedek, et. al., "Precise Nuclear Resonance Thermometer", The Review of Scientific Instruments, v.28, No. 2, pp. 92-95, Feb. 1957.

Ernst, "Magnetic Resonance with Stochastic Excitation", Journal of Magnetic Resonance 3, pp. 10-27, 1970.

Klainer, et. al., "Founder Transform Nuclear Quadrupole Resonance Spectroscopy", Fourier, Hadamard, and Hilbert Transforms in Chemistry, pp. 147-182, 1982.

* cited by examiner

USE OF MULTIPLE SENSORS IN A NUCLEAR QUADROPOLE RESONANCE DETECTION SYSTEM TO IMPROVE MEASUREMENT SPEED

This application claims the benefit if U.S. Provisional Application No. 60/529,991, filed on Dec. 15, 2003, which is incorporated in its entirety as a part hereof for all purposes.

FIELD OF THE INVENTION

This invention relates to the use of multiple sensors to improve measurement speed of a nuclear quadrupole resonance detection system.

BACKGROUND OF THE INVENTION

The use of nuclear quadrupole resonance (NQR) as a means of detecting explosives and other contraband has been recognized for some time; see e.g., T. Hirshfield et al, *J. Molec. Struct.* 68, 63 (1980); A. N. Garroway et al, *Proc. SPIE* 2092, 318 (1993); and A. N. Garroway et al, *IEEE Trans. on Geoscience and Remote Sensing* 39, 1108 (2001). NQR provides some distinct advantages over other detection methods. NQR requires no external magnet such as required by nuclear magnetic resonance. NQR is sensitive to the compounds of interest, i.e. there is a specificity of the NQR frequencies.

One technique for measuring NQR in a sample is to place the sample within a solenoid coil that surrounds the sample. The coil provides a radio frequency (RF) magnetic field that excites the quadrupole nuclei in the sample and results in their producing their characteristic resonance signals. This is the typical apparatus configuration that might be used for scanning mail, baggage or luggage.

There is also need for a NQR detector that permits detection of NQR signals from a source outside the detector, e.g. a wand detector, that could be passed over persons or containers as is done with existing metal detectors. Problems associated with such detectors using conventional systems are the decrease in detectability with distance from the detector coil, and the associated equipment needed to operate the system.

A detection system can have one or more coils that both transmit and receive, or it can have separate coils that only transmit and only receive. A transmit, or transmit and receive, coil of an NQR detection system provides a radio frequency (RF) magnetic field that excites the quadrupole nuclei in the sample and results in their producing their characteristic resonance signals that the receive, or transmit and receive, coil (i.e. the sensor) detects. The NQR signals have low intensity and short duration.

The transmit, receive, or transmit and receive coil preferably has a high quality factor (Q). The transmit, receive, or transmit and receive coil has typically been a copper coil and therefore has a Q of about $10^2$. It can be advantageous to use a transmit, receive, or transmit and receive coil made of a high temperature superconductor (HTS) rather than copper since the HTS self-resonant coil has a Q of the order of $10^3$-$10^6$. The large Q of the HTS self-resonant coil produces large magnetic field strengths during the RF transmit pulse, and does so at lower RF power levels. This dramatically reduces the amount of transmitted power required to produce NQR signals for detection, and thereby reduces the size of the RF power supply sufficiently so that it can be run on portable batteries.

The large Q of the HTS self-resonant coil also plays an important role during the receive time. In view of the low intensity NQR signal, it is important to have a signal-to-noise ratio (S/N) as large as possible. As the signal-to-noise (S/N) ratio is proportional to the square root of Q, the use of the HTS self-resonant coil results in an increase in S/N by a factor of 10-100 over that of the copper system. These advantages during both the transmit and the receive times enable a detector configuration that is small and portable.

The NQR frequencies are temperature dependent; see e.g. T. Kushida et al, *Phys. Rev.* 104, 1364 (1956); J. Vanier, *Can. J. Phys.* 38, 1397 (1960); and David H. Smith et al, *J. Chem. Phys.* 41, 2403 (1964). When the temperature of the source of the NQR is known only within a range $\Delta T$, the NQR frequency $f_{NQR}$ is known only within a range of frequencies $\Delta f_{NQR}$. Since it is advantageous as described above for a sensor, i.e. a receive coil, to have a high Q and therefore a narrow bandpass, use of a single sensor requires a number of measurements, and a tuning to a new resonance frequency after each measurement, in order to scan the range of frequencies $\Delta f_{NQR}$. This process is time-consuming. Accuracy and speed of measurement are important features of any detection system used for scanning a potential source of explosives, drugs or other contraband.

An object of the present invention is therefore to provide a method for increasing the speed of a NQR detection system for scanning a potential source of NQR when the frequency of the nuclear quadrupole resonance is not precisely known.

SUMMARY OF THE INVENTION

This invention provides a method for improving the measurement speed of a nuclear quadrupole resonance detection system when the frequency of the nuclear quadrupole resonance of any quadrupole nuclei in the sample to be scanned is known only within a range of frequencies $\Delta f_{NQR}$, wherein $f_1$ and $f_2$ are the frequencies corresponding to the end points of the range of frequencies $\Delta f_{NQR}$.

One embodiment of this invention consequently is, in a system for scanning a sample to detect nucelear quadrupole resonance, where the frequency of the nuclear quadrupole resonance of any quadrupole nuclei in the sample is known only within a range of frequencies $\Delta f_{NQR}$, and wherein $f_1$ and $f_2$ are the frequencies corresponding to the end points of the range of frequencies $\Delta f_{NQR}$, a method for improving the measurement speed of the system by:

a) providing n sensors to detect the nuclear quadrupole resonance signal, wherein the n sensors are tuned to m different resonance frequencies, at least two of which are between $f_1$ and $f_2$, and wherein n is greater than 1, and $2 \leq m \leq n$;

b) irradiating the sample with an RF signal that has frequencies corresponding to the sensor resonance frequencies between $f_1$ and $f_2$ to excite any nuclear quadrupole resonance having a resonance frequency at one or more of the sensor resonance frequencies between $f_1$ and $f_2$;

c) detecting a nuclear quadrupole resonance signal, if any, using the sensors with resonance frequencies between $f_1$ and $f_2$;

d) retuning then sensors to p different resonance frequencies, at least two of which are between $f_1$ and $f_2$, wherein at least two of the resonance frequencies between $f_1$ and $f_2$ are different from any of the previously tuned resonance frequencies between $f_1$ and $f_2$, and wherein $2 \leq p \leq n$;

e) irradiating the sample with an RF signal that has frequencies corresponding to the retuned sensor resonance frequencies between $f_1$ and $f_2$ to excite any nuclear quadrupole resonance having a resonance frequency at one or more of the retuned frequencies between $f_1$ and $f_2$;

f) detecting a nuclear quadrupole resonance signal, if any, using the sensors with retuned resonance frequencies between $f_1$ and $f_2$; and g) repeating steps (d), (e) and (f) until the whole range of frequencies between $f_1$ and $f_2$ has been scanned, wherein p can have the same or different values each time step (d) is repeated.

The method of the invention further comprises the additional steps of halting the scanning of the sample if a nuclear quadrupole resonance signal is detected at any time during the scanning of the sample or sounding an alarm if a nuclear quadrupole resonance signal is detected at any time during the scanning of the sample or both.

The invention also provides a nuclear quadrupole resonance detection system for scanning a sample when the frequency of the nuclear quadrupole resonance of any quadrupole nuclei in the sample is known only within a range of frequencies $\Delta f_{NQR}$, wherein $f_1$ and $f_2$ are the frequencies corresponding to the end points of the range of frequencies $\Delta f_{NQR}$.

Another embodiment of this invention is consequently a nuclear quadrupole resonance detection system for scanning a sample in which the frequency of the nuclear quadrupole resonance of any quadrupole nuclei in the sample lie within a range of frequencies $\Delta f_{NQR}$, wherein $f_1$ and $f_2$ are the frequencies corresponding to the end points of the range of frequencies $\Delta f_{NQR}$, that includes a) n sensors to detect the nuclear quadrupole resonance signal, wherein n is greater than 1;

b) means to (i) tune then sensors to m different resonance frequencies at least two of which are between $f_1$ and $f_2$, wherein $2 \leq m \leq n$; (ii) retune then sensors to p different resonance frequencies at least two of which are between $f_1$ and $f_2$, wherein at least two of the retuned resonance frequencies between $f_1$ and $f_2$ are different from any of the previously tuned or retuned resonance frequencies between $f_1$ and $f_2$, wherein $2 \leq p \leq n$, and wherein p has the same or different values each time the n sensors are retuned; and (iii) repeatedly retune the n sensors to p different resonance frequencies until the whole range of frequencies between $f_1$ and $f_2$ has been scanned; and c) means for irradiating the sample with an RF signal that has (i) frequencies corresponding to the originally tuned resonance frequencies between $f_1$ and $f_2$, or (ii) frequencies corresponding to any retuned resonance frequencies between $f_1$ and $f_2$, to excite any nuclear quadrupole resonance having a resonance frequency at one or more of the resonance frequencies between $f_1$ and $f_2$.

The nuclear quadrupole resonance detection system of the invention further comprises means for halting the scanning of the sample if the nuclear quadrupole resonance signal is detected at any time during the scanning of the sample, or an alarm that is sounded if the nuclear quadrupole resonance signal is detected at any time during the scanning of the sample, or both of these features.

Preferably, the majority of the m different resonance frequencies and the p different resonance frequencies of the n sensors are between $f_1$ and $f_2$. More preferably, all of the m different resonance frequencies and all of the p different resonance frequencies are between $f_1$ and $f_2$. Most preferably, m=n and p=n.

Preferably, the n sensors are used solely to detect the nuclear quadrupole resonance signal and a separate coil is used to transmit the RF signal to irradiate the sample. Preferably, the n sensors are high temperature superconductor coils. Preferably, the transmit coil is a shielded loop resonator coil made of copper, silver or aluminum.

This invention for improving the measurement speed of a nuclear quadrupole resonance detection system is especially important when the nuclear quadrupole resonance detection system is used for detecting the nuclear quadrupole resonance of explosives (such as RDX or PETN), drugs or other contraband.

DETAILED DESCRIPTION OF THE PREFERRED EMBODIMENTS

When it is desired to detect the presence of a substance, there are some circumstances under which the NQR frequency of the substance to be detected is not precisely known. For example, an NQR frequency, $f_{NQR}$, varies with the temperature of the source of the NQR. In some instances the temperature of a known or potential source of NQR is known only within a range $\Delta T$, where $T_1$ and $T_2$ are the temperatures corresponding to the end points of the temperature range $\Delta T$ so that $\Delta T = T_2 - T_1$. In these instances the NQR frequency $f_{NQR}$ is known only within a range of frequencies $\Delta f_{NQR}$, where $f_1$ and $f_2$ are the frequencies corresponding to the end points of the range of frequencies $\Delta f_{NQR}$ so that $\Delta f_{NQR} = f_1 - f_2$. The change in $f_{NQR}$ with temperature at a given temperature is given by the derivative $df_{NQR}/dT$.

Over a sufficiently small temperature range $df_{NQR}/dT$ can be approximated as being constant. With this approximation, for the range of temperatures of interest, i.e. $\Delta T$, the uncertainty in the temperature of the source of the NQR, $\Delta f_{NQR} = (df_{NQR}/dT) \Delta T$. With a single sensor with a bandwidth $\Delta f$, the number of measurements required to scan the range of frequencies $\Delta f_{NQR}$ is of the order of $\Delta f_{NQR}/\Delta f$, i.e. $(df_{NQR}/dT) \Delta T/\Delta f$.

As an example, the $v_\_$ NQR frequency of sodium nitrate is about 3605 MHz at room temperature, and changes by about −1 kHz/K. Therefore, when the source temperature is known only within a 20K range, a search over a frequency range of $\Delta f_{NQR}$ of about 20 kHz is required to be sure that the NQR frequency has been included in the scan of the detection system. Use of a single HTS sensor with a bandwidth of 1 kHz requires on the order of 20 measurements to scan the 20 kHz range of frequencies. Between measurements, the resonance frequency of the sensor must be tuned to a new frequency. If each individual measurement and frequency tuning requires 0.5 s, the total time to scan would be on the order of 10 s.

The instant invention provides a method for increasing the measurement speed of a NQR detection system for scanning a potential source of NQR when the source temperature is not precisely known, and also provides a NQR detection system that can accomplish these increased measurement speeds. The use of the method or the apparatus of this invention reduces the measurement time by a factor of the order of 1/n, where n is the number of sensors. If the n sensors are not all scanned simultaneously, the full decrease of 1/n in the measurement time will not be realized. If n is on the order of $\Delta f_{NQR}/\Delta f$, the whole range of frequencies between $f_1$ and $f_2$ can be scanned simultaneously if the RF signal spans the whole range of frequencies between $f_1$ and $f_2$.

The n sensors can be tuned and retuned in different ways, i.e. according to different strategies, in different embodiments of the invention. At least two of the n sensors must have resonance frequencies between $f_1$ and $f_2$ in order to reduce the time of measurement compared to that experienced when using a single sensor. The number of sensors n can take on any value greater than 1 that is dictated by the particular use. A practical upper limit to n would usually be of the order of $\Delta f_{NQR}/\Delta f$.

The n sensors are first tuned to m different resonance frequencies, wherein $2 \leq m \leq n$. At least two of the m resonance frequencies are between $f_1$ and $f_2$. If no NQR signal is detected when these sensor resonance frequencies between $f_1$ and $f_2$ are scanned, the n sensors are retuned to p different resonance frequencies, wherein $2 \leq p \leq n$. At least two of the p resonance frequencies are between $f_1$ and $f_2$. If no NQR signal is detected when these retuned sensor resonance frequencies between $f_1$ and $f_2$ are scanned, the n sensors are again retuned to p different resonance frequencies wherein p has the same or different values each time the n sensors are retuned. The retuning of the n sensors and the scanning is repeated until the whole range of frequencies between $f_1$ and $f_2$ has been scanned, or a nuclear quadrupole resonance signal has been detected.

It a preferred embodiment, each time the n sensors are retuned to p different frequencies, at least two of the retuned resonance frequencies between $f_1$ and $f_2$ are different from any of the originally tuned or previously retuned resonance frequencies between $f_1$ and $f_2$.

The value of p can be the same or different each time the retuning is repeated. The values of m and p, and the number of resonance frequencies between $f_1$ and $f_2$, will vary depending on the circuitry used to tune and retune the n sensors and the particular use. Preferably, the majority (such as more than 50, 60, 70 or 80 percent) of the m different resonance frequencies and the p different resonance frequencies of the n sensors are between $f_1$ and $f_2$. More preferably, all of the m different resonance frequencies, and all of the p different resonance frequencies, are between $f_1$ and $f_2$. Preferably, m and p are a large fraction of n such as at least 60%, at least 70% or at least 80% of n. More preferably, m=n and p=n.

Most preferably, the n sensors are tuned to n different resonance frequencies all of which are between $f_1$ and $f_2$. If no NQR signal is detected when these n frequencies are scanned, the n sensors are retuned to n different resonance frequencies all of which are between $f_1$ and $f_2$, and all of which are different from any of the previously tuned resonance frequencies of the n sensors. These retuned resonance frequencies are then scanned. This retuning is continued until either the whole range of frequencies between $f_1$ and $f_2$ has been scanned, or a nuclear quadrupole resonance signal has been detected.

Preferably, the resonance frequency of each sensor differs from the resonance frequency of the sensor with the nearest higher resonance frequency by an amount equal to or greater than the bandwidth $\Delta f$ of a sensor, each of which may be, and typically is, the same. The bandwidth $\Delta f$ is the full width at half height bandwidth of the sensor. The bandwidths of the HTS coils preferred as sensors are essentially the same from coil to coil.

A power supply can be used to provide the RF signal with frequencies corresponding to the resonance frequencies of those sensors having resonance frequencies between $f_1$ and $f_2$ to excite any nuclear quadrupole resonance having a resonance frequency at one or more of those frequencies. As used herein by "a frequency corresponding to the resonance frequency of a sensor" is meant a frequency within the bandwidth $\Delta f$ of a sensor and not necessarily the exact resonance frequency or mid-point of the bandwidth of the sensor. The RF signal can consist essentially of only the resonance frequencies of the n sensors, or can encompass all the frequencies between $f_1$ and $f_2$.

In various alternative embodiments, the scanning of the sample can be halted, or an alarm can be sounded, if the nuclear quadrupole resonance signal is detected at any time during the scanning of the sample. Means for halting the scanning of the sample may include a circuit that will deactivate and re-set the transmit coil if the nuclear quadrupole resonance signal is detected.

Although the same coils can be used to transmit the RF signal and receive any NQR signal, separate coils preferably are used as excitation coils to transmit the RF signal and as sensors to detect any NQR signal. When two coupled high temperature superconductor self-resonant coils are used as a sensor, the resonance frequency of the fundamental symmetric mode of the two coupled high temperature superconductor self-resonant coils can be varied by mechanically displacing one coil with respect to the other. The means to tune and retune the resonance frequency of sensors thus includes the mechanical displacement of one coil with respect to another as described above. Means for mechanically displacing one coil with respect to another can include, for example, a threaded drive shaft that can be operated manually or electrically by an actuator; or an electromechanical device such as a piezo electric transducer, a stepping motor, or a dc drive motor.

Alternatively, for a sensor comprised of a high temperature superconductor self-resonant coil or two coupled high temperature superconductor self-resonant coils, the means for tuning and retuning the resonance frequency of a sensor may include a circuit. One such circuit is comprised of a single loop or coil to inductively couple the circuit to the high temperature superconductor self-resonant sensor, a reactance in series with the single loop or coil, and means to enable the reactance to be connected to and disconnected from the single loop or coil. The single loop or coil can be made of a regular conductor such as copper or a high temperature superconductor. The reactance can be an inductance, capacitance or combination of both. Preferably, the means to enable the reactance to be connected to and disconnected from the single loop or coil may include at least one mechanical switch or electrical switch such as a diode. Preferably, the reactance can be varied so that the resonance frequency can be adjusted to more than one frequency.

In one embodiment in which a variable reactance is provided, the reactance may include two or more capacitors in parallel, each of which can be individually connected to or disconnected from the single loop or coil. Alternatively, a variable reactance may include two or more inductors in series, each of which can be individually connected to or disconnected from the single loop or coil by a mechanical or electrical switch that can short-circuit the inductor, and thereby remove it, or essentially remove it, from the circuit. A circuit comprised of a variable reactance can be used to tune more than one sensor. As a result, the means to tune and retune the resonance frequency of each of the n sensors may include one or more circuits each of which is comprised of a variable reactance.

The means to tune and retune the resonance frequencies of the n sensors may also include an automated controller with a memory function that will record the quantity and/or identity of each of the various frequencies as originally tuned, and as retuned in each retuning step. This will enable tracking which frequencies the sensors have been tuned to in previous tuning or retuning steps.

As mentioned above, it is often advantageous to be able to fine-tune the resonance frequency of the coil. One means for accomplishing such tuning is to use two coupled high temperature superconductor self-resonant coils. The resonance frequency of the fundamental symmetric mode of the two coupled high temperature superconductor self-resonant coils can be varied by mechanically displacing one coil with respect to the other, and these coupled coils may be used as the HTS sensor. Preferably, the two coils are planar, i.e. surface, coils. Each planar coil may have a HTS coil configuration on only one side of the substrate, or may have essentially identical HTS coil configurations on both sides of the substrate. Most preferably, the HTS sensors are each comprised of a high temperature superconductor self-resonant planar coil or two coupled high temperature superconductor self-resonant planar coils.

Preferably, then sensors are high temperature superconductor (HTS) coils. A high temperature superconductor coil is preferably in the form of a self-resonant planar coil, i.e. a surface coil, with a coil configuration of HTS on one or both sides of a substrate. High temperature superconductors are those that superconduct above 77K. The high temperature superconductors used to form the HTS self-resonant coil are preferably selected from the group consisting of $YBa_2Cu_3O_7$, $Tl_2Ba_2CaCu_2O$, $TlBa_2Ca_2Cu_3O_9$, (TlPb) $Sr_2CaCu_2O_7$ and (TlPb) $Sr_2Ca_2Cu_3O_9$. Most preferably, the high temperature superconductor is $YBa_2Cu_3O_7$ or $Tl_2Ba_2CaCu_2O_8$.

The HTS self-resonant coil can be formed by various known techniques. Preferably, a planar coil is formed by first depositing HTS layers on both sides of a single crystal substrate. In a preferred technique for forming a $Tl_2Ba_2CaCu_2O_8$ coil, the HTS layers are formed directly on a single crystal $LaAlO_3$ substrate or on a $CeO_2$ buffer layer on a single crystal sapphire ($Al_2O_3$) substrate. An amorphous precursor layer of Ba:Ca:Cu oxide about 500 nm thick and with a stoichiometry of about 2:1:2 is deposited by off-axis magnetron sputtering from a Ba:Ca:Cu oxide target. The precursor film is then thallinated by annealing it in air for about 45 minutes at 850° C. in the presence of a powder mixture of $Tl_2Ba_2Ca_2Cu_3O_{10}$ and $Tl_2O_3$. When this powder mixture is heated, $Tl_2O$ evolves from the powder mixture, diffuses to the precursor film and reacts with it to form the $Tl_2Ba_2CaCu_2O_8$ phase.

The sample is then coated with photoresist on both sides and baked. A coil design mask is prepared. The design mask is then centered on the photoresist covering the $Tl_2Ba_2CaCu_2O_8$ film on the front side of the substrate and exposed to ultraviolet light. If the coil is to have the same HTS pattern on both sides of the substrate, the design mask is then centered on the photoresist covering the $Tl_2Ba_2CaCu_2O_8$ film on the back side of the substrate and exposed to ultraviolet light. The resist is then developed on both sides of the substrate and the portion of the $Tl_2Ba_2CaCu_2O_8$ film exposed when the resist is developed is etched away by argon beam etching. The remaining photoresist layer is then removed by an oxygen plasma. The result is the desired HTS coil. If two coupled high temperature superconductor self-resonant coils are to be used as the sensor, a second coil can be produced using the same technique.

The means for irradiating the sample with an RF signal may include transmit coils that can be made of copper, silver or aluminum. Preferably, the transmit coil is a copper, silver or aluminum coil in the form of a shielded loop-resonator (SLR) coil. SLR's have been developed to eliminate the detuning effect of the electrical interaction between the coil and the surrounding material. Most preferably, the means used to irradiate the sample with the RF signal is a SLR copper transmit coil.

The detected NQR signals may be processed on circuitry as conventionally used in the art. If one or more HTS coils are used, they may be cooled by a cryogenic apparatus as conventionally used in the art such as a cryo cooler that is capable of reaching at least the temperature of liquid nitrogen.

What is claimed is:

1. In a system for scanning a sample to detect nuclear quadrupole resonance, where the frequency of the nuclear quadrupole resonance of any quadrupole nuclei in the sample is known only within a range of frequencies $\Delta f_{NQR}$, and wherein $f_1$ and $f_2$ are the frequencies corresponding to the end points of the range of frequencies $\Delta f_{NQR}$, a method for improving the measurement speed of the system, comprising:
   a) providing n sensors to detect the nuclear quadrupole resonance signal,
      wherein the n sensors are high temperature superconductor self-resonant planar coils used solely to detect the nuclear quadrupole resonance signal, and
      wherein the n sensors are tuned to m different resonance frequencies, at least two of which are between $f_1$ and $f_2$, and
      wherein n is greater than 1 and $2 \leq m \leq n$;
   b) irradiating the sample with an RF signal that has frequencies corresponding to the sensor resonance frequencies between $f_1$ and $f_2$ to excite any nuclear quadrupole resonance having a resonance frequency at one or more of the sensor resonance frequencies between $f_1$ and $f_2$;
   c) detecting a nuclear quadrupole resonance signal, if any, using the sensors with resonance frequencies between $f_1$ and $f_2$;
   d) retuning the n sensors to p different resonance frequencies, at least two of which are between $f_1$ and $f_2$, wherein at least two of the resonance frequencies between $f_1$ and $f_2$ are different from any of the previously tuned resonance frequencies between $f_1$ and $f_2$, and where $2 \leq p \leq n$,
      wherein the resonance frequency of each of the n sensors is tuned and retuned using n circuits, one for each of the n sensors, wherein each circuit of the n circuits is comprised of a single loop or coil to inductively couple the circuit to the high temperature superconductor self-resonant sensor, a variable reactance in series with the single loop or coil, and means to connect the variable reactance to, and disconnect the variable reactance from, the single loop or coil;
   e) irradiating the sample with an RF signal that has frequencies corresponding to the retuned sensor resonance frequencies between $f_1$ and $f_2$ to excite any nuclear quadrupole resonance having a resonance frequency at one or more of the retuned frequencies between $f_1$ and $f_2$;

f) detecting a nuclear quadrupole resonance signal to indicate the presence of quadrupole nuclei in the sample, if any, using the sensors with retuned resonance frequencies between $f_1$ and $f_2$; and g) repeating steps (d), (e) and (f) until the whole range of frequencies between $f_1$ and $f_2$ has been scanned, wherein p can have the same or different values each time step (d) is repeated.

2. The method of claim 1, wherein the variable reactance is comprised of two or more capacitors in parallel, each of which capacitors can be individually connected to or disconnected from the single loop or coil by a mechanical or electrical switch.

3. The method of claim 1, wherein the variable reactance is comprised of two or more inductors in series, each of which inductors can be individually connected to or disconnected from the single loop or coil by a mechanical or electrical switch that can short-circuit the inductor and thereby essentially remove it from the circuit.

4. The nuclear quadrupole resonance detection system of claim 1, wherein the sample comprises explosives, drugs or other contraband.

5. In a system for scanning a sample to detect nuclear quadrupole resonance, where the frequency of the nuclear quadrupole resonance of any quadrupole nuclei i the sample is known only within a range of frequencies $\Delta f_{NQR}$, and wherein $f_1$ and $f_2$ are the frequencies corresponding to the end points of the range of frequencies $\Delta f_{NQR}$, a method for improving the measurement speed of the system, comprising:

a) providing n sensors to detect the nuclear quadrupole resonance signal,
      wherein the n sensors are high temperature superconductor self-resonant planar coils used solely to detect the nuclear quadrupole resonance signal, and
      wherein the n sensors are tuned to m different resonance frequencies, at least two of which are between $f_1$ and $f_2$, and
      wherein n is greater than 1 and $2 \leq m \leq n$;

b) irradiating the sample with an RF signal that has frequencies corresponding to the sensor resonance frequencies between $f_1$ and $f_2$ to excite any nuclear quadrupole resonance having a resonance frequency at one or more of the sensor resonance frequencies between $f_1$ and $f_2$;

c) detecting a nuclear quadrupole resonance signal, if any, using the sensors with resonance frequencies between $f_1$ and $f_2$;

d) retuning the n sensors to p different resonance frequencies, at least two of which are between $f_1$ and $f_2$, wherein at least two of the resonance frequencies between $f_1$ and $f_2$ are different from any of the previously tuned resonance frequencies between $f_1$ and $f_2$, and wherein $2 \leq p \leq n$,
      wherein the resonance frequency of each of the n sensors is tuned and retuned using one or more circuits, wherein each the circuits is comprised of a variable reactance;

e) irradiating the sample with an RF signal that has frequencies corresponding to the retuned sensor resonance frequencies between $f_1$ and $f_2$ to excite any nuclear quadrupole resonance having a resonance frequency at one or more of the retuned frequencies between $f_1$ and $f_2$;

f) detecting a nuclear quadrupole resonance signal to indicate the presence of quadrupole nuclei in the sample, if any, using the sensors with retuned resonance frequencies between $f_1$ and $f_2$; and g) repeating steps (d), (e) and (f) until the whole range of frequencies between $f_1$ and $f_2$ has been scanned, wherein p can have the same or different values each time step (d) is repeated.

6. The nuclear quadrupole resonance detection system of claim 5, wherein the sample comprises explosives, drugs or other contraband.

7. In a system for scanning a sample to detect nuclear quadrupole resonance, where the frequency of the nuclear quadrupole resonance of any quadrupole nuclei in the sample is known only within a range of frequencies $\Delta f_{NQR}$, and wherein $f_1$ and $f_2$ are the frequencies corresponding to the end points of the range of frequencies $\Delta f_{NQR}$, a method for improving the measurement speed of the system, comprising:

a) providing n sensors to detect the nuclear quadrupole resonance signal,
      wherein the n sensors are each comprised of two coupled high temperature superconductor self-resonant planar coils used solely to detect the nuclear quadrupole resonance signal, and
      wherein the n sensors are tuned to m different resonance frequencies, at least two of which are between $f_1$ and $f_2$, and
      wherein n is greater than 1 and $2 \leq m \leq n$;

b) irradiating the sample with an RF signal that has frequencies corresponding to the sensor resonance frequencies between $f_1$ and $f_2$ to excite any nuclear quadrupole resonance having a resonance frequency at one or more of the sensor resonance frequencies between $f_1$ and $f_2$;

c) detecting a nuclear quadrupole resonance signal, if any, using the sensors with resonance frequencies between $f_1$ and $f_2$;

d) retuning the n sensors to p different resonance frequencies, at least two of which are between $f_1$ and $f_2$, wherein at least two of the resonance frequencies between $f_1$ and $f_2$ are different from any of the previously tuned resonance frequencies between $f_1$ and $f_2$, and wherein $2 \leq p \leq n$,
      wherein the resonance frequency of each of the n sensors is tuned and retuned using n circuits, one for each of the n sensors, wherein each circuit of the n circuits is comprised of a single loop or coil to inductively couple the circuit to the high temperature superconductor self-resonant sensor, a variable reactance in series with the single loop or coil, and means to enable the variable reactance to be connected to and disconnected from the single loop or coil;

e) irradiating the sample with an RF signal that has frequencies corresponding to the retuned sensor resonance frequencies between $f_1$ and $f_2$ to excite any nuclear quadrupole resonance having a resonance frequency at one or more of the retuned frequencies between $f_1$ and $f_2$;

f) detecting a nuclear quadrupole resonance signal to indicate the presence of quadrupole nuclei in the sample, if any, using the sensors with retuned resonance frequencies between $f_1$ and $f_2$; and g) repeating steps (d), (e) and (f) until the whole range of frequencies between $f_1$ and $f_2$ has been scanned, wherein p can have the same or different values each time step (d) is repeated.

8. The method of claim 7, wherein the variable reactance is comprised of two or more capacitors in parallel, each of which capacitors can be individually connected to or disconnected from the single loop or coil by a mechanical or electrical switch.

9. The method of claim 7, wherein the variable reactance is comprised of two or more inductors in series, each of which inductors can be individually connected to or disconnected from the single loop or coil by a mechanical or electrical switch that can short-circuit the inductor and thereby essentially remove it from the circuit.

10. The nuclear quadrupole resonance detection system of claim 7, wherein the sample comprises explosives, drugs or other contraband.

11. In a system for scanning a sample to detect nuclear quadrupole resonance, where the frequency of the nuclear quadrupole resonance of any quadrupole nuclei in the sample is known only within a range of frequencies $\Delta f_{NQR}$, and wherein $f_1$ and $f_2$ are the frequencies corresponding to the end points of the range of frequencies $\Delta f_{NQR}$, a method for improving the measurement speed of the system, comprising:
  a) providing n sensors to detect the nuclear quadrupole resonance signal,
    wherein the n sensors are each comprised of two coupled high temperature superconductor self-resonant planar coils used solely to detect the nuclear quadrupole resonance signal, and
    wherein the n sensors are tuned to m different resonance frequencies, at least two of which are between $f_1$ and $f_2$, and
    wherein n is greater than 1 and $2 \leq m \leq n$;
  b) irradiating the sample with an RF signal that has frequencies corresponding to the sensor resonance frequencies between $f_1$ and $f_2$ to excite any nuclear quadrupole resonance having a resonance frequency at one or more of the sensor resonance frequencies between $f_1$ and $f_2$;
  c) detecting a nuclear quadrupole resonance signal, if any, using the sensors with resonance frequencies between $f_1$ and $f_2$;
  d) retuning the n sensors to p different resonance frequencies, at least two of which are between $f_1$ and $f_2$, wherein at least two of the resonance frequencies between $f_1$ and $f_2$ are different from any of the previously tuned resonance frequencies between $f_1$ and $f_2$, and wherein $2 \leq p \leq n$,
    wherein the resonance frequency of each of the n sensors is tuned and retuned using one or more circuits, wherein each of the circuits is comprised of a variable reactance;
  e) irradiating the sample with an RF signal that has frequencies corresponding to the retuned sensor resonance frequencies between $f_1$ and $f_2$ to excite any nuclear quadrupole resonance having a resonance frequency at one or more of the retuned frequencies between $f_1$ and $f_2$;
  f) detecting a nuclear quadrupole resonance signal to indicate the presence of quadrupole nuclei in the sample, if any, using the sensors with retuned resonance frequencies between $f_1$ and $f_2$; and
  g) repeating steps (d), (e) and (f) until the whole range of frequencies between $f_1$ and $f_2$ has been scanned, wherein p can have the same or different values each time step (d) is repeated.

12. The nuclear quadrupole resonance detection system of claim 11, wherein the sample the sample comprises explosives, drugs or other contraband.

13. A nuclear quadrupole resonance detection system for scanning a sample in which the frequency of the nuclear quadrupole resonance of any quadrupole nuclei in the sample lie within a range of frequencies $\Delta f_{NQR}$, wherein $f_1$ and $f_2$ are the frequencies corresponding to the end points of the range of frequencies $\Delta f_{NQR}$, comprising:
  a) n sensors to detect the nuclear quadrupole resonance signal, wherein n is greater than 1, wherein the n sensors are high temperature superconductor self-resonant planar coils which solely detect the nuclear quadrupole resonance signal;
  b) means for
    (i) tuning the n sensors to m different resonance frequencies at least two of which are between $f_1$ and $f_2$, wherein $2 \leq m \leq n$,
    (ii) retuning the n sensors to p different resonance frequencies at least two of which are between $f_1$ and $f_2$, wherein at least two of the retuned resonance frequencies between $f_1$ and $f_2$ are different from any of the previously tuned or retuned resonance frequencies between $f_1$ and $f_2$, wherein $2 \leq p \leq n$, and wherein p has the same or different values each time the n sensors are retuned, and
    (iii) repeatedly retuning the n sensors to p different resonance frequencies until the whole range of frequencies between $f_1$ and $f_2$ has been scanned,
    wherein the means to tune and retune the resonance frequency of each of the n sensors comprises n circuits, one for each of the n sensors, wherein each of the n circuits is comprised of a single loop or coil to inductively couple the circuits to the high temperature superconductor self-resonant sensor, a variable reactance in series with the single loop or coil, and means to connect the variable reactance to, and disconnect the variable reactance from, the single loop or coil; and
  c) means for irradiating the sample with an RF signal that has
    (i) frequencies corresponding to the originally tuned resonance frequencies between $f_1$ and $f_2$, or
    (ii) frequencies corresponding to any retuned resonance frequencies between $f_1$ and $f_2$,
    thereby to excite any nuclear quadrupole resonance having a resonance frequency at one or more of the resonance frequencies between $f_1$ and $f_2$.

14. The nuclear quadrupole resonance detection system of claim 13, wherein the variable reactance is comprised of two or more capacitors in parallel, each of which capacitors can be individually connected to or disconnected from the single loop or coil by a mechanical or electrical switch.

15. The nuclear quadrupole resonance detection system of claim 13, wherein the variable reactance is comprised of two or more inductors in series, each of which inductors can be individually connected to or disconnected from the single loop or coil by a mechanical or electrical switch to short-circuit the inductor and essentially remove it from the circuit.

16. The nuclear quadrupole resonance detection system of claim 13, wherein the sample the sample comprises explosives, drugs or other contraband.

17. A nuclear quadrupole resonance detection system for scanning a sample in which the frequency of the nuclear quadrupole resonance of any quadrupole nuclei in the sample lie within a range of frequencies $\Delta f_{NQR}$, wherein $f_1$ and $f_2$ are the frequencies corresponding to the end points of the range of frequencies $\Delta f_{NQR}$, comprising:

a) n sensors to detect the nuclear quadrupole resonance signal, wherein n is greater than 1, wherein the n sensors are high temperature superconductor self-resonant planar coils which solely detect the nuclear quadrupole resonance signal;

b) means for
   (i) tuning the n sensors to m different resonance frequencies at least two of which are between $f_1$ and $f_2$, wherein $2 \leq m \leq n$,
   (ii) retuning the n sensors to p different resonance frequencies at least two of which are between $f_1$ and $f_2$, wherein at least two of the retuned resonance frequencies between $f_1$ and $f_2$ are different from any of the previously tuned or retuned resonance frequencies between $f_1$ and $f_2$, wherein $2 \leq p \leq n$, and wherein p has the same or different values each time the n sensors are retuned, and
   (iii) repeatedly retuning the n sensors to p different resonance frequencies until the whole range of frequencies between $f_1$ and $f_2$ has been scanned,
   wherein the means to tune and retune the resonance frequency of each of the n sensors comprises one or more circuits, each of which circuits is comprised of a variable reactance; and c) means for irradiating the sample with an RF signal that has
   (i) frequencies corresponding to the originally tuned resonance frequencies between $f_1$ and $f_2$, or
   (ii) frequencies corresponding to any retuned resonance frequencies between $f_1$ and $f_2$,
   thereby to excite any nuclear quadrupole resonance having a resonance frequency at one or more of the resonance frequencies between $f_1$ and $f_2$.

18. The nuclear quadrupole resonance detection system of claim 17, wherein the sample the sample comprises explosives, drugs or other contraband.

19. A nuclear quadrupole resonance detection system for scanning a sample in which the frequency of the nuclear quadrupole resonance of any quadrupole nuclei in the sample lie within a range of frequencies $\Delta f_{NQR}$, wherein $f_1$ and $f_2$ are the frequencies corresponding to the end points of the range of frequencies $\Delta f_{NQR}$, comprising:

a) n sensors to detect the nuclear quadrupole resonance signal, wherein n is greater than 1, wherein the n sensors are each comprised of two coupled high temperature superconductor self-resonant planar coils which solely detect the nuclear quadrupole resonance signal;

b) means for
   (i) tuning the n sensors to m different resonance frequencies at least two of which are between $f_1$ and $f_2$, wherein $2 \leq m \leq n$,
   (ii) retuning the n sensors to p different resonance frequencies at least two of which are between $f_1$ and $f_2$, wherein at least two of the retuned resonance frequencies between $f_1$ and $f_2$ are different from any of the previously tuned or retuned resonance frequencies between $f_1$ and $f_2$, wherein $2 \leq p \leq n$, and wherein p has the same or different values each time the n sensors are retuned, and
   (iii) repeatedly retuning the n sensors to p different resonance frequencies until the whole range of frequencies between $f_1$ and $f_2$ has been scanned,
   wherein the means to tune and retune the resonance frequency of each of the n sensors comprises n circuits, one for each of the n sensors, wherein each of the n circuits is comprised of a single loop or coil to inductively couple the circuit to the high temperature superconductor self-resonant sensor, a variable reactance in series with the single loop or coil, and means to connect the variable reactance to, and disconnect the variable reactance from, the single loop or coil; and c) means for irradiating the sample with an RF signal that has
   (i) frequencies corresponding to the originally tuned resonance frequencies between $f_1$ and $f_2$, or
   (ii) frequencies corresponding to any retuned resonance frequencies between $f_1$ and $f_2$,
   thereby to excite any nuclear quadrupole resonance having a resonance frequency at one or more of the resonance frequencies between $f_1$ and $f_2$.

20. The nuclear quadrupole resonance detection system of claim 19, wherein the variable reactance is comprised of two or more capacitors in parallel, each of which capacitors can be individually connected to or disconnected from the single loop or coil by a mechanical or electrical switch.

21. The nuclear quadrupole resonance detection system of claim 19, wherein the variable reactance is comprised of two or more inductors in series, each of which inductors can be individually connected to or disconnected from the single loop or coil by a mechanical or electrical switch to short-circuit the inductor and essentially remove it from the circuit.

22. The nuclear quadrupole resonance detection system of claim 19, wherein the sample the sample comprises explosives, drugs or other contraband.

23. A nuclear quadrupole resonance detection system for scanning a sample in which the frequency of the nuclear quadrupole resonance of any quadrupole nuclei in the sample lie within a range of frequencies $\Delta f_{NQR}$, wherein $f_1$ and $f_2$ are the frequencies corresponding to the end points of the range of frequencies $\Delta f_{NQR}$, comprising:

a) n sensors to detect the nuclear quadrupole resonance signal, wherein n is greater than 1, wherein the n sensors are each comprised of two coupled high temperature superconductor self-resonant planar coils which solely detect the nuclear quadrupole resonance signal;

b) means for
   (i) tuning the n sensors to m different resonance frequencies at least two of which are between $f_1$ and $f_2$, wherein $2 \leq m \leq n$,
   (ii) retuning the n sensors to p different resonance frequencies at least two of which are between $f_1$ and $f_2$, wherein at least two of the retuned resonance frequencies between $f_1$ and $f_2$ are different from any of the previously tuned or retuned resonance frequencies between $f_1$ and $f_2$, wherein $2 \leq p \leq n$, and wherein p has the same or different values each time the n sensors are retuned, and
   (iii) repeatedly retuning the n sensors to p different resonance frequencies until the whole range of frequencies between $f_1$ and $f_2$ has been scanned,
   wherein the means to tune and retune the resonance frequency of each of the n sensors comprises one or more circuits, each of which circuits is comprised of a variable reactance; and c) means for irradiating the sample with an RF signal that has
   (i) frequencies corresponding to the originally tuned resonance frequencies between $f_1$ and $f_2$, or (ii) frequencies corresponding to any retuned resonance frequencies between $f_1$ and $f_2$, thereby to excite any nuclear quadrupole resonance having a resonance frequency at one or more of the resonance frequencies between $f_1$ and $f_2$.

24. The nuclear quadrupole resonance detection system of claim 23, wherein the sample the sample comprises explosives, drugs or other contraband.

* * * * *